(12) United States Patent
Kölbel et al.

(10) Patent No.: US 7,998,189 B2
(45) Date of Patent: Aug. 16, 2011

(54) CURVABLE STENT-GRAFT AND APPARATUS AND FITTING METHOD

(75) Inventors: Tilo Kölbel, Malmo (SE); Martin Malina, Malmo (SE)

(73) Assignee: Cook Medical Technologies LLC, Bloomington, IN (US)

( * ) Notice: Subject to any disclaimer, the term of this patent is extended or adjusted under 35 U.S.C. 154(b) by 35 days.

(21) Appl. No.: 12/287,676

(22) Filed: Oct. 10, 2008

(65) Prior Publication Data

US 2010/0094401 A1    Apr. 15, 2010

(51) Int. Cl.
*A61F 2/06* (2006.01)
(52) U.S. Cl. ............................ 623/1.13; 623/1.23
(58) Field of Classification Search ......... 623/1.12–1.13, 623/1.16, 1.23, 2.36–2.37
See application file for complete search history.

(56) References Cited

U.S. PATENT DOCUMENTS

| 5,713,948 | A * | 2/1998 | Uflacker | 623/1.23 |
| 6,974,471 | B2 | 12/2005 | Van Schie et al. | |
| 7,771,455 | B2 * | 8/2010 | Ken | 606/213 |
| 2001/0037142 | A1* | 11/2001 | Stelter et al. | 623/1.13 |
| 2002/0007208 | A1* | 1/2002 | Strecker | 623/1.12 |
| 2003/0088305 | A1* | 5/2003 | Van Schie et al. | 623/1.12 |
| 2004/0054396 | A1* | 3/2004 | Hartley et al. | 623/1.13 |
| 2005/0125031 | A1* | 6/2005 | Pipenhagen et al. | 606/213 |

\* cited by examiner

*Primary Examiner* — David H Willse
*Assistant Examiner* — Tiffany Shipmon
(74) *Attorney, Agent, or Firm* — Richard J. Godlewski (57) ABSTRACT

A stent-graft (100) is provided with a tightenable loop element (122) having a first end terminated in a self-tightening knot (142) and a second end (138) which is received in and can slide in the knot (142). The loop (122) is fitted to the stent-graft (100) in a manner as to cause curvature of the stent-graft (100) upon tightening of the loop. An introducer assembly is also disclosed which includes a cannula (132, 150) within which a pull cord (136) and release wire (134) are located.

11 Claims, 7 Drawing Sheets

CURVABLE STENT-GRAFT AND APPARATUS AND FITTING METHOD

FIELD OF THE INVENTION

The present invention relates to an implantable medical device such as a stent-graft, stent or similar device, as well as to apparatus for and a method of fitting such a device into a lumen of a patient, particularly into a highly curved lumen such as the aortic arch and into locations which provide little room for error in the placement of the device, such as lumens having short necks of healthy vascular wall.

BACKGROUND OF THE INVENTION

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient, aortic prostheses, for example, being commonly fed through the femoral artery. A generally accepted method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into a highly curved vessel such as the aortic arch.

Even though such a procedure is possible into the aortic arch, it is mired in difficulties as a result of the tight curvature of the aorta in this location. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus a less than effective treatment. Furthermore, as a result of the non-optimal placement of the stent-graft using known procedures, it is necessary to have a reasonable length of healthy vascular wall in order to provide a seal around the proximal end of the stent-graft. This limits the application of such stent-grafts, in particular for the treatment of aneurysms close to a branch vessel and to conditions where there is at least a certain length of healthy vessel wall tissue, thus making the procedure not available to treat a reasonable proportion of medical cases.

In addition, in some instances at least, a part of the proximal end of the stent-graft can remain loosely located in the vessel, leading to premature fatigue failure as well as thrombus effects.

Attempts have been made to resolve these difficulties. For instance, in the applicant's U.S. Pat. No. 6,974,471, mechanisms are described for imparting a curvature to the stent-graft at the moment of its deployment.

The deployment of stent-grafts and other devices, particularly in the aortic arch, in lumens having short necks of healthy vascular wall and other difficult pathologies also requires very precise placement of the device to ensure a good coupling to healthy tissue and in particular a coupling which has longevity and which provides a fluid-tight seal with the vessel wall. Prior art systems do allow for a certain amount of coarse re-positioning of the device. However, if the device is not fitted precisely in the correct location, the procedure may need to be repeated, for example by withdrawing the device back into its delivery introducer (where this is possible) and starting the deployment operation afresh. Repeating the procedure increases operating time, trauma to the patient and still does not guarantee a successful outcome. In some instances, it is necessary to abort the procedure.

SUMMARY OF THE INVENTION

The present invention seeks to provide an improved implantable medical device and an improved system for and method of fitting a stent-graft or other device to a patient.

According to an aspect of the present invention, there is provided an implantable medical device including a compressible and curvable structure; a tightenable loop of thread, the tightenable loop including a first end closed in a knot and a second end passing through the knot and able to slide therein at least in a loop tightening direction, the loop being fitted to the device such that tightening of the loop causes the device to curve.

The loop enables the medical device to be compressed on one side so as to cause it to curve. In the case of a stent-graft, the device can be made to curve so as to fit the curvature of the aortic arch, for instance, to provide much better positioning of the proximal end of the device and thus better sealing of the device to the internal walls of the vessel.

Preferably, the knot is a self-tightening knot, which ensures that the medical device retains a minimum curvature even after deployment. By self-tightening it is meant that the knot is self-locking.

In the preferred embodiment, the device is a stent-graft.

In an embodiment, the tightenable loop is positioned around at least two stents of the implantable medical device.

According to another aspect of the present invention, there is provided an introducer assembly suitable for deploying in a vessel of a patient an implantable medical device provided with a compressible and curvable structure, a tightenable loop of thread, the loop including a first end closed in a knot and a second end passing through the knot and able to slide therein at least in a loop tightening direction, the tightenable loop being fitted to the device such that tightening of the loop causes the device to curve; the assembly including a cannula provided with a lumen therethrough; a pull cord within the lumen, the pull cord being provided with a looped end; a release element in the lumen, which release element is operable to cooperate with the pull cord and the loop of thread on the implantable medical device for use in pulling on the loop of thread and thereby for causing the implantable medical device to curve.

The cannula preferably acts in a manner analogous to a Bowden cable.

Preferably, the release element includes control rod or wire.

Advantageously, the tightenable loop includes a tied loop at a free end thereof, the tied loop cooperating with the release element and the pull cord.

Preferably, the release element is operable to release the tied loop of the tightenable loop from the pull cord.

In an embodiment, the pull cord is provided with a looped end engageable with a looped end on the second end of the tightenable loop, the looped end of the pull cord being able to be carried by the release element and releasable by withdrawal of the release element so as to detach the tightenable loop from the introducer.

According to another aspect of the present invention, there is provided a method of deploying an implantable medical device provided with a compressible and curvable structure, a loop of thread including a first end closed in a knot and a second end passing through the knot and able to slide therein at least in a loop tightening direction, the loop being fitted to the device such that tightening of the loop causes the device to curve; the implantable medical device being carried on an introducer; the method including the steps of releasing the implantable medical device from the introducer; pulling on the loop of thread, thereby to cause the implantable medical device to curve; releasing coupling of the pull cord; and removing the introducer assembly from the patient.

Preferably, the method includes the step of allowing for the loop of thread to self-lock, thereby to keep the implantable medical device in the curved condition.

DESCRIPTION OF THE DRAWINGS

Embodiments of the present invention are described below, by way of example only, with reference to the accompanying drawings, in which.

DESCRIPTION OF THE PREFERRED EMBODIMENT

For the purposes of this disclosure, when used in connection with description of a stent-graft or other implantable medical device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

Figure 1:
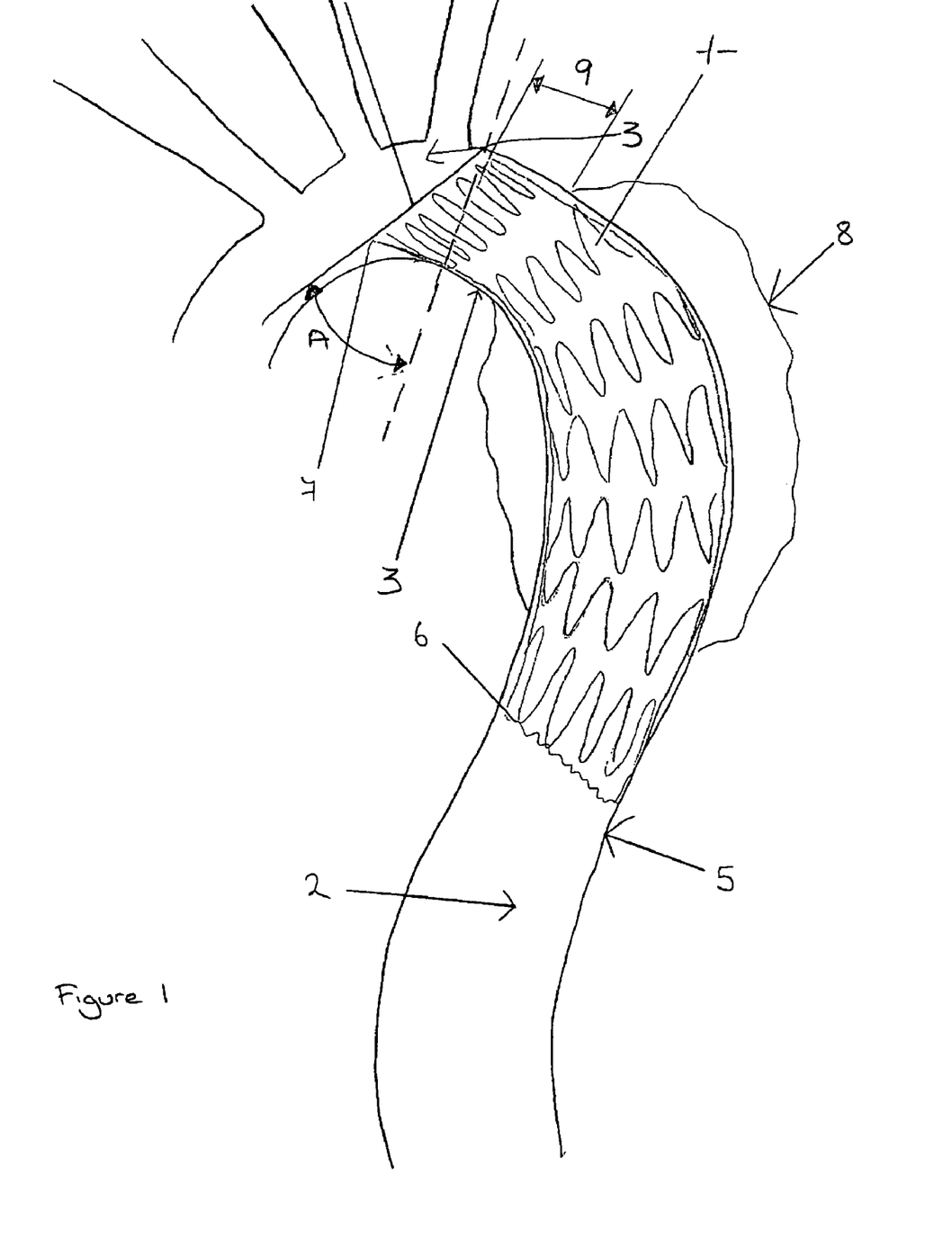
FIG. 1 shows an example of stent-graft deployed in the aortic arch by a conventional introducer system.

Referring to FIG. 1, there is shown an example of deployment of a stent-graft 1 within the aorta 2 of a patient for the treatment of, for example, an aneurysm 8. In this particular example, the stent-graft extends part-way into the aortic arch 3 at its proximal end 4, down to the thoracic aorta 5 at its distal end 6. The curvature of the aortic arch 3, coupled with use of a conventional introducer system which follows the arch 3 by being bent thereby, can cause the proximal end 4 of the stent-graft 1 to be located incorrectly, that is not to have its opening perpendicular with the vessel at that position. As a result, the inner side 7 of the stent-graft 1 stands proud of the vessel wall, being spaced therefrom. In particular, the proximal end 4 of the stent graft will typically tend to lie at an angle A which deviates from the perpendicular line B. The resultant gap between the inner side 7 and the aortic wall provides a path for leakage of blood and thus an incomplete seal, which can lead to failure of the stent-graft in achieving its intended function. In practice, such imprecise deployment results in it being necessary to have a relatively long neck 9 to achieve a reliable seal between the stent-graft 1 and the vessel wall as well as limiting the application of such implantable medical devices to areas lumens which have no more than a certain curvature, in some cases thus excluding the aortic arch. Thus, medical conditions which do not have a sufficient length of adequate neck 9, that is of healthy vessel wall, or which have too great a curvature cannot at present be treated.

In addition to these problems, the end 7 of the stent-graft tends to flap in the force of blood flow, leading to possible stent-graft collapse, fatigue wear and possibly rupture, as well as to thrombus formation.

Figure 2:
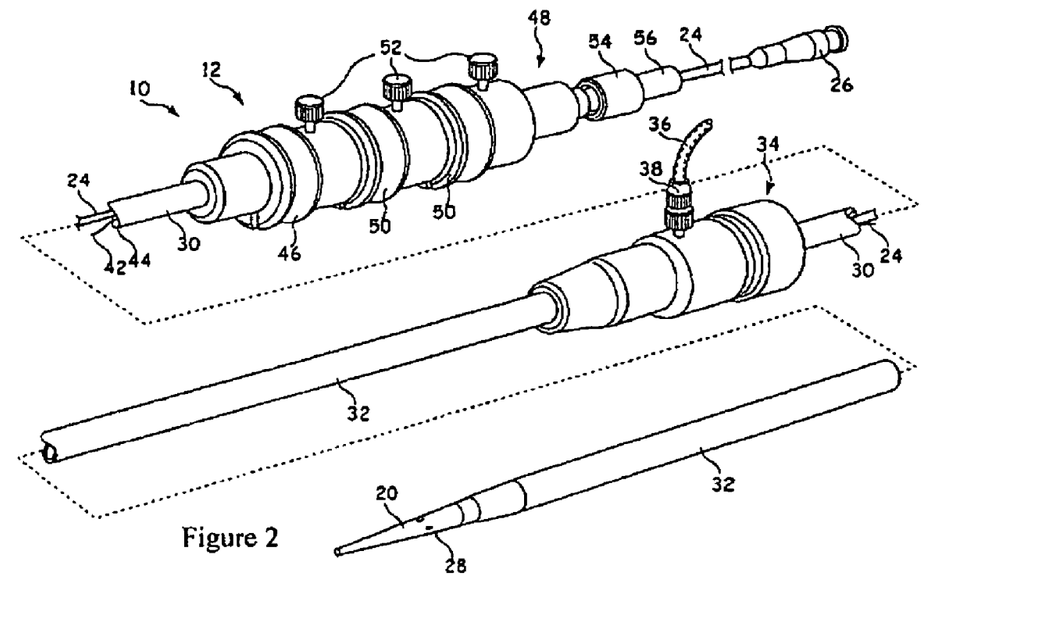
FIGS. 2 and 3 are perspective views of an example of introducer system which can be used with the present invention.
Figure 3:
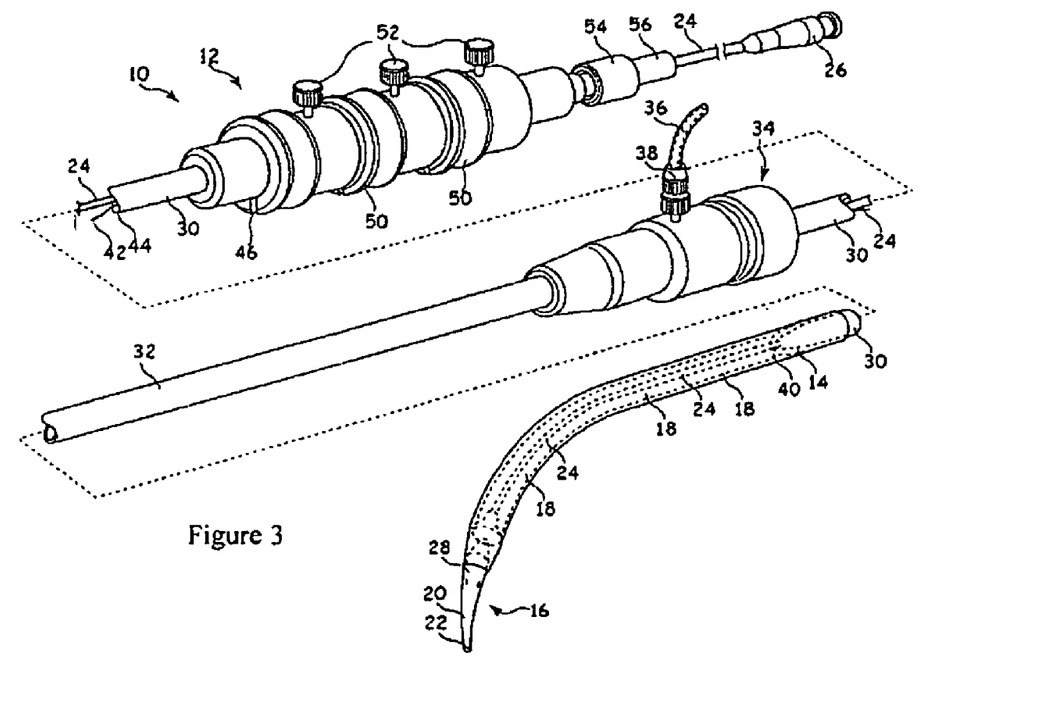

Referring now to FIGS. 2 and 3, there is shown an example of introducer of the type used in the deployment of stent-grafts of the form shown in FIG. 1. The introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire 25 of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

As will be apparent in particular from FIG. 3, the distal end of the introducer is flexible, so as to be able to follow a tortuous path of a patient's vasculature, as well as in some applications to locate a stent-graft in a curved portion of a lumen such as the aortic arch. The distal end curves, however, by being pulled into this configuration as a result of curving of the guide wire, which is itself urged into a curved shape by the curvature of the lumen. As a result of this, the distal end of the introducer tends to follow the outside of any curve. When deployment occurs in such a situation, as it does in the aortic arch for example, the stent-graft can become improperly located, as in the example of FIG. 1.

Figure 4:
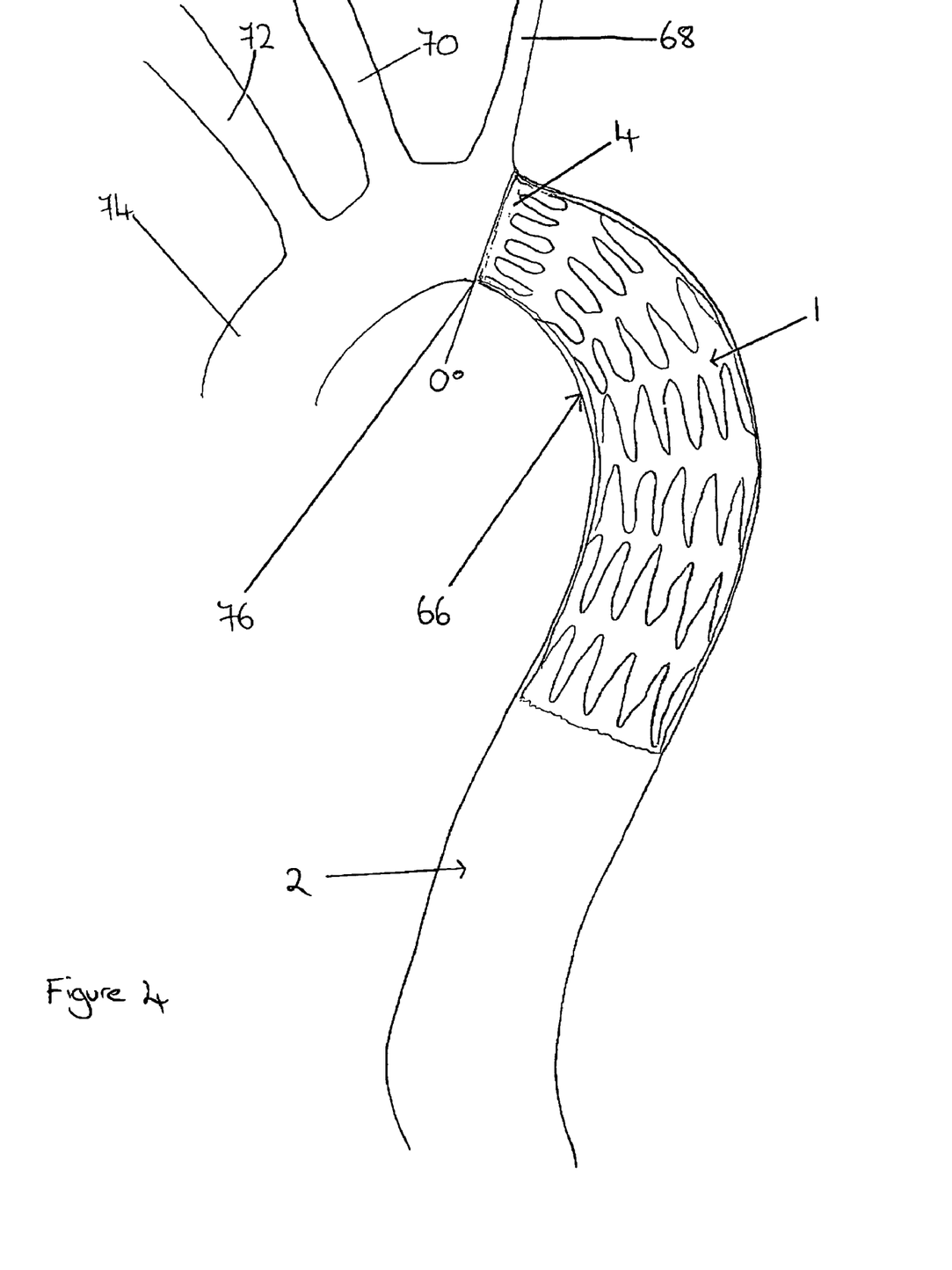
FIG. 4 is a view similar to that of FIG. 1 showing the ideal placement of a stent-graft within the aortic arch.

The optimal configuration for the stent-graft is shown in FIG. 4. As can be seen, the stent-graft 1 is properly deployed in an aorta 2 of a patient. The proximal end 4 of the stent-graft 1 is positioned in the aortic arch 66, just short of the left subclavian artery 68, in this example, although in some circumstances may extend to beyond the left subclavian artery 68, or even beyond the left common carotid artery 70 and the brachiocephalic artery 72 and into the ascending aorta 74. Fenestrated or branched stent-grafts for such applications are known in the art.

It will be noted that the proximal end 4 lies correctly in FIG. 4, so as to be substantially perpendicular to the vessel. In this orientation, it properly seals to the vessel wall around all of its circumference, including at the radially internal side 76, leaving no gap for blood leakage.

Precise and reliable placement of the proximal end 4 of the stent-graft 1 allows this to be fitted in a much shorter neck length of vessel wall compared to the less reliable prior art systems.

The present invention seeks to address the problems encountered with prior art introducer systems in a way which can enhance the fitting of the stent-graft into a lumen, particularly at the aortic arch and other highly curved regions of vasculature.

Figure 5:
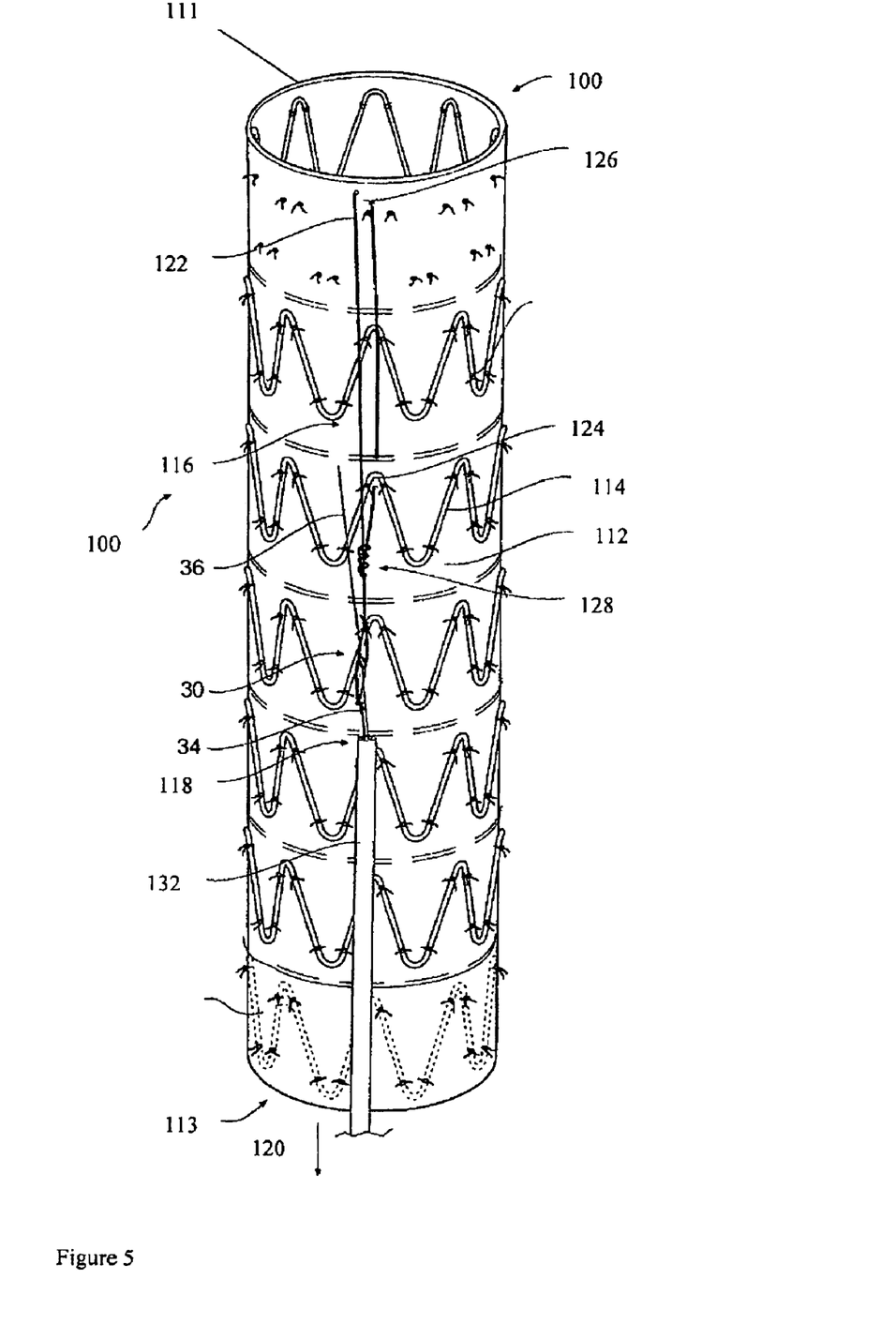
FIG. 5 is a schematic diagram showing the preferred embodiment of curvable implantable medical device.

Referring now to FIG. 5, there is shown the preferred embodiment of curvable stent graft 100. It will be seen that the stent graft 100 comprises a tubular body 112 of a biocompatible graft material. The tubular body 112 has a proximal end 111 and a distal end 113. The tubular body 112 has a plurality of self-expanding stents 114 spaced therealong. A curving device, generally shown as 116, is mounted longitudinally along the length of the tubular body 112 at its proximal end 111 and being looped around two or more stent rings 114.

A pulling arrangement, shown generally as 118, is releasably connected to the curving device thread 116 and extends distally as shown by the arrow 120.

The curving device 116 includes a loop of thread 122 engaged into the tubular body at a first position 124 which is spaced distally from the proximal end 111 of the stent graft 10, in this embodiment adjacent an apex of the third stent ring 114 of the stent graft 100. The region between the first position 124 and the proximal end 111 is the region which it is desired to curve to cause the stent graft 100 to conform more precisely with a curved portion of a patient's vasculature.

The loop of thread 122 is loops into the tubular body 112 at a second position 126 adjacent the proximal end 111 of the stent graft. The loop 122 extends distally to engage with the pulling arrangement 118 at a third position 127. A releasable connection generally shown as 130 between the loop of thread 122 and the pulling arrangement 118 is discussed in more detail in connection with FIGS. 6A and 6B.

The loop of thread 122 includes a gripping arrangement which allows the loop 122 to be pulled distally, in particular a self-locking knot 128. The knot 128 allows the thread to be pulled therethrough in a distal direction but does not allow movement of the thread in the opposite direction. Thus, the loop 116 can be tightened but not loosened. As a result, once the loop 116 has been tightened, the stent graft 100 will maintain the curved shape produced buy the tightening loop and will not extend back to a straight configuration.

The pulling arrangement 118 could be described as a form of Bowden cable arrangement. More specifically, the pulling arrangement 118 includes a cannula 132 through which extends a pull thread 134 and a release wire 136.

Figure 6A:
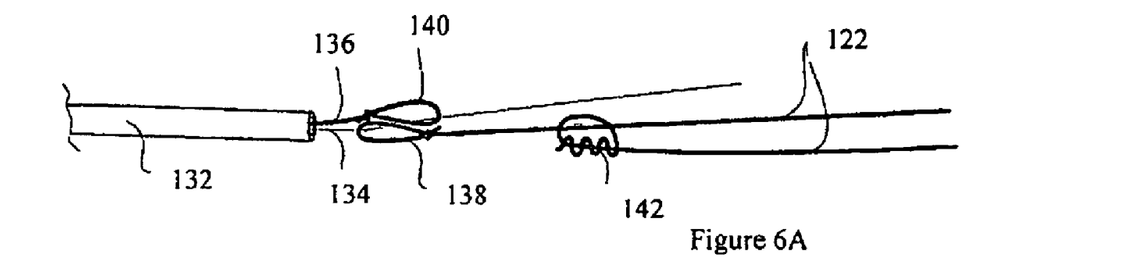
FIGS. 6A and 6B show the preferred embodiment of suture loop tightening device both before and after the suture loop has been tightened.
Figure 6B:
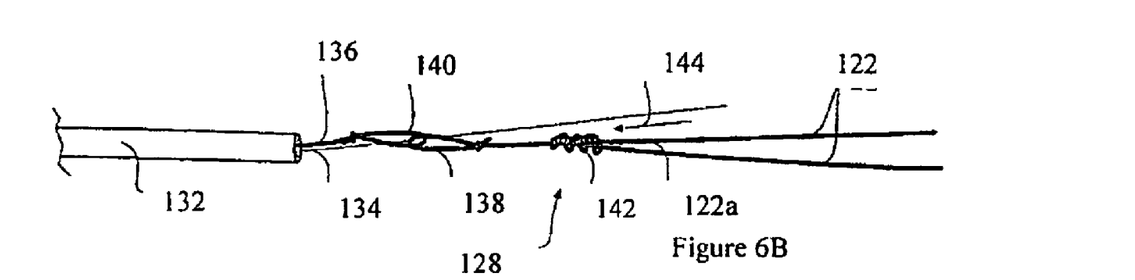

The releasable connection generally shown as 130 between the curve forming arrangement 116 and the pulling arrangement 118 is shown FIGS. 6A and 6B. FIG. 6A shows the arrangement in a loose configuration, whereas FIG. 6B shows the arrangement once it has been tightened and once it has pulled back on the loop 122.

At the free end of the thread forming the tightenable loop 112 there is provided a closed tie loop 138. Similarly, the distal end of the pull thread 136 ends in a closed tie loop 140. The closed tie loops 138, 140 are coupled to one another by feeding one of these loops 138, 140 into the other 138, 140. The release wire 134 is then fed through the fed-through loop such that the latter loop cannot slide back out of the other loop as it is restrained by the wire 134. For this purpose the wire 134 is preferably substantially rigid and for this purpose may be formed of a metal or metal alloy, steel, Nitinol and the like. One embodiment provides a 0.018 inch diameter wire 134.

The other end of the tightenable loop 122 is provided with a self-tightening knot 142. This may be a half-blood knot or any other known self-tightening or self-locking knot.

When the pull cord 134 is pulled backwards, that is in a proximal direction along the introducer, the tie loops 138, 140 are caused to tighten to one another by virtue of the release wire 134 keeping them coupled together. Further pulling of the pull cord 134 produces a pulling force on the loop 122, in particular on its side 122a, such that this will begin to tighten. So doing will at the same time tighten the knot 142.

Figure 7:
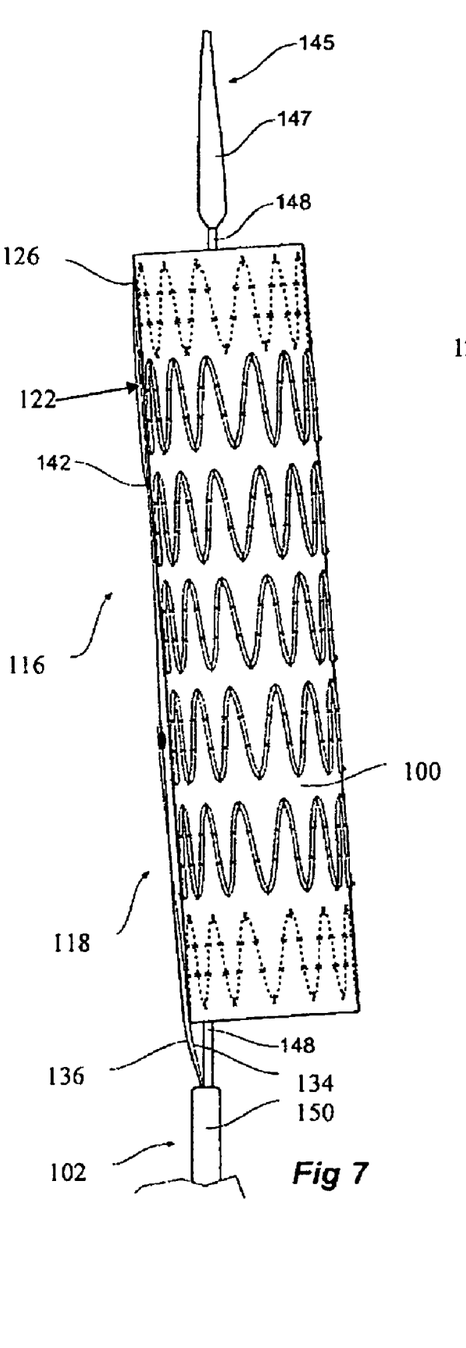
FIG. 7 shows the implantable medical device of FIG. 5 located on an introducer in a condition ready for curving.
Figure 8:
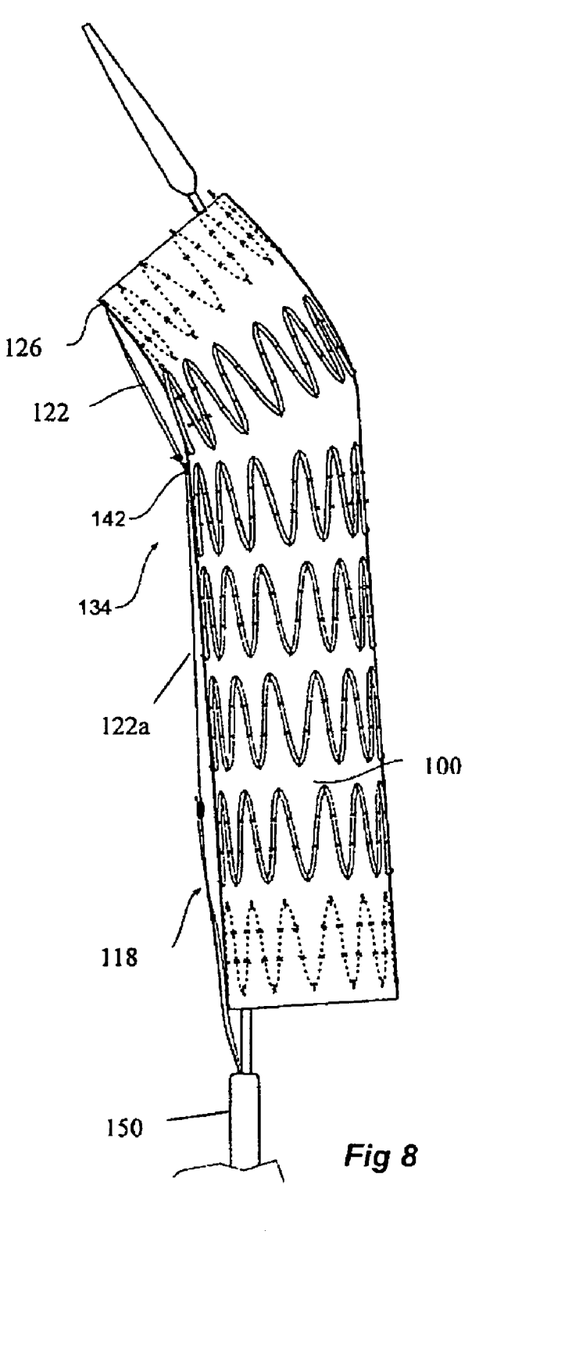
FIG. 8 is a view similar to FIG. 7, in which the implantable medical device has been curved.

Referring now to FIGS. 7 and 8, there is shown the operation the curve forming arrangement disclosed herein. In FIGS. 7 and 8 the stent graft 100 is releasably retained to the distal end of an introducer assembly 102 and in these drawings is shown in an expanded state after a sheath (not shown) has been retracted.

The delivery device 102 is of generally conventional form and includes a distal end 145 to be deployed into a patient in use and a proximal, external manipulation, end (not shown) which remains outside the patient. The distal end 145 includes a nose cone dilator 147 mounted onto a guide wire catheter 148. The stent graft 100 is positioned coaxially around the guide wire catheter and releasably fastened to it by retention means (not shown) of conventional form. The delivery device 102 also includes a deployment catheter or push rod 150 which extends to a handle (not shown) at the proximal end of the delivery device.

The curve forming arrangement 116 is mounted longitudinally along the length of the stent graft 100 while the pulling arrangement 118 is shown in this embodiment to form part of the introducer 102. In particular, in this embodiment, the catheter or cannula 132 is the same component as the catheter or push rod 150 within which the inner catheter 148 is located. The release wire 134 and pull cord 136 are located within the catheter 150 and extend up to the tightenable loop 122, in particular to its closed tie loop 138.

In the view of FIG. 7, the stent graft 100 has been released from the introducer such that it has expanded to its normal in situ size but the pull cord 136 has not yet been pulled and the stent graft 100 retains its unbiased straight form. At this time the curving elements are as shown in FIG. 6A.

Upon pulling of the pull cord 136 in a proximal direction of the introducer, that is out of the patient, the tightenable loop 122 begins to tighten and thus pull the proximal end 126 of the stent graft 100 backwards. This causes the stent graft 100 to curve as shown in FIG. 8 as a result of there being a constraining action on only one side of the stent graft 100.

It will be appreciated from FIG. 8 in particular that as the tightenable loop 122 is pulled, the knot 146 will tend to be pulled in a proximal direction of the stent graft (that is towards its front end) but that the knot 146 will only travel until the point of insertion of the thread 122 into the graft material.

Figure 9:
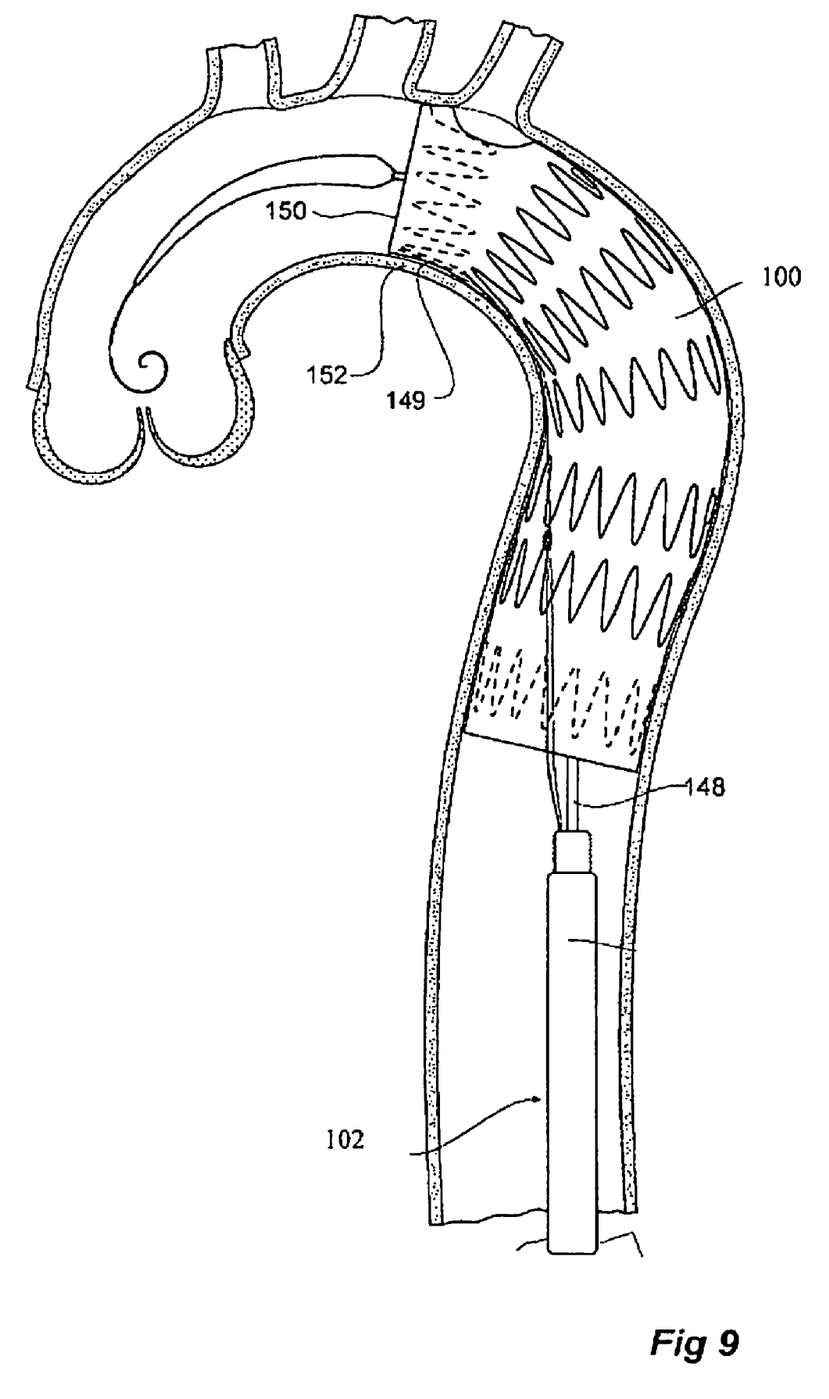
FIG. 9 shows the implantable medical device of FIG. 5 fitted into the aortic arch of a patient.

With reference also to FIG. 9, this shows schematically the thoracic arch of the aorta of a patient with stent graft 100 in position. It will be noted that the sheath 154 of the delivery device 102 has been retracted and the stent graft 100 has expanded out to the wall of the aorta. It will also be noted that the stent graft 100 is curved to conform with the shape of the vasculature by the use of the curving apparatus and in particular that the inside portion 149 of the proximal end 150 is held against the inside curve of the thoracic aorta 152 thereby giving a good seal.

More specifically, the operation of curving the proximal end 150 of the stent-graft 100 is intended to conform the shape of the stent-graft 100 to the shape of the lumen within which it is placed. For example, for deployment in the aortic arch, as shown in FIGS. 4 and 9, the stent-graft 100 is curved, by pulling on the suture loop 122, to an extent comparable to the curvature of the aortic arch. So doing better orients the proximal end 150 to the vessel wall, so as to achieve a placement of this end as close as possible to parallel with the vessel wall, such that the opening of the stent-graft at its proximal end 150 is substantially perpendicular to the vessel wall. This optimizes the seal of the proximal end 150 of the stent-graft 100 to the vessel wall and also allows the fitting of a stent-graft in vessels having only a short neck of healthy vessel wall tissue.

Correct orientation of the device in the patient's lumen can be achieved by the use of one or more radio opaque markers, such as gold markers, (not shown). Furthermore, in some embodiments the distal end of the introducer and in particular of the dilator tip 147 could be curved to assist in the deployment procedure. The curving arrangement 116 would be located within the introducer at the inner side of that curve so as to follow this curvature. This can assist in correction orientation of the stent-graft and in particular of the curving arrangement 116.

An additional advantage of the embodiments described below, in particular in connection with the feature of having the loop 122 extend substantially to the proximal end 111 of the stent graft 100, is that the loop when tightened will tend to pull the inner edge of the proximal end 111 towards the vessel wall, thus improving the seal. The outer edge of the proximal end 111 of the stent graft will tend to a straighter configuration and will therefore seal well against the vessel wall.

Once the stent graft 100 has been curved and placed as desired, the release wire 134 is pulled in a proximal direction of the introducer, that is backwards. This allows the two closed tie loops 138 and 140 to separate from one another and thus for the pull cord 134 to be separated from the tightenable loop 122.

The introducer assembly can then be removed from the patient, leaving only the curving arrangement 116 in position on the stent-graft 100 with the knot 142 locking the loop 122 in position.

A characteristic of self-tightening knots is that they allow, in this example, the end 122a to be pulled through the knot so as to reduce the length of the loop 122 and thus to pull the distal end 126 of the stent-graft 100 into a curved configuration. The knot 142 then locks the loop in place, to prevent the end 126 from sliding in the opposite, loop loosening, direction. Such a knot fixes the stent-graft 100 in the selected angle of curvature and does not allow this to increase.

It will be appreciated that the various features taught herein could be used in combination, as described above, but could equally be used by themselves in other medical devices and introducer systems.

Although the above-described embodiments use a loop device 116 with a self-tightening knot, it is envisaged that a slip knot could be used instead, which will allow the stent graft 10, 100 to flex towards a straighter configuration after deployment. This will give the stent graft more flexibility to flex with the vessel but will still retain a good seal at its proximal end as the latter will tend to retain its position after placement.

What is claimed is:

1. An implantable medical device having a longitudinal axis and including a compressible and curvable structure; a tightenable loop of thread fitted to the medical device and coupled thereto at two longitudinally spaced locations of the device, the tightenable loop including a first end closed in a knot and a second end passing through the knot and able to slide therein at least in a loop tightening direction wherein tightening of the loop by pulling on said second end pulls said longitudinally spaced locations towards one another and thereby to cause the device to curve away from the longitudinal axis of the device.

2. An implantable medical device according to claim 1, wherein the knot is a self-tightening knot.

3. An implantable medical device according to claim 1, wherein the tightenable loop is positioned around at least two stents of the implantable medical device.

4. An implantable medical device according to claim 1, wherein the device is a stent-graft.

5. An introducer assembly suitable for deploying in a vessel of a patient an implantable medical device having a longitudinal axis and provided with a compressible and curvable structure, a tightenable loop of thread fitted to the medical device and coupled thereto at two longitudinally spaced locations of the device, the loop including a first end closed in a knot and a second end passing through the knot and able to slide therein at least in a loop tightening direction, wherein tightening of the loop by pulling on said second end pulls said longitudinally spaced locations towards one another and thereby to cause the device to curve away from the longitudinal axis of the device; the assembly including a cannula provided with a lumen therethrough; a pull cord within the lumen, the pull cord being provided with a looped end; a release element in the lumen, which release element is operable to cooperate with the pull cord and the loop of thread on the implantable medical device for use in pulling on the loop of thread so as to tighten said loop, wherein said tightening of the loop pulls said longitudinally spaced locations of the device towards one another and thereby, to cause the implantable medical device to curve away from the longitudinal axis of the device.

6. An introducer assembly according to claim 5, wherein the release element includes control rod or wire.

7. An introducer assembly according to claim 5, wherein the tightenable loop includes a tied loop at a free end thereof, the tied loop cooperating with the release element and the pull cord.

8. An introducer assembly according to claim 7, wherein the release element is operable to release the tied loop of the tightenable loop from the pull cord.

9. An introducer assembly according to claim 7, wherein the pull cord is provided with a looped end engageable with a looped end on the second end of the tightenable loop, the looped end of the pull cord being able to be carried by the release element and releasable by withdrawal of the release element so as to detach the tightenable loop from the introducer.

10. A method of deploying an implantable medical device, said device having a longitudinal axis and being provided with a compressible and curvable structure, a loop of thread including a first end closed in a knot and a second end passing through the knot and able to slide therein at least in a loop tightening direction, the loop being fitted to the device such that tightening of the loop causes the device to curve away from the longitudinal axis of the device; the implantable medical device being carried on an introducer according to claim 5; the method including the steps of releasing the implantable medical device from the introducer; pulling on the loop of thread, thereby to cause the implantable medical device to curve away from the longitudinal axis of the device; releasing coupling of the pull cord; and removing the introducer assembly from the patient.

11. A method according to claim 10, including the step of allowing for the loop of thread to self-lock, thereby to keep the implantable medical device in the curved condition.

* * * * *